(12) United States Patent
Hossainy

(10) Patent No.: US 7,699,889 B2
(45) Date of Patent: *Apr. 20, 2010

(54) POLY(ESTER AMIDE) BLOCK COPOLYMERS

(75) Inventor: Syed Faiyaz Ahmed Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 5 days.

This patent is subject to a terminal disclaimer.

(21) Appl. No.: 12/114,645

(22) Filed: May 2, 2008

(65) Prior Publication Data

US 2008/0206306 A1  Aug. 28, 2008

Related U.S. Application Data

(63) Continuation of application No. 11/023,837, filed on Dec. 27, 2004, now Pat. No. 7,419,504.

(51) Int. Cl.
| | |
|---|---|
| A61L 9/16 | (2006.01) |
| C08G 69/44 | (2006.01) |
| A61L 31/16 | (2006.01) |
| A61L 31/10 | (2006.01) |
| A61K 47/48 | (2006.01) |

(52) U.S. Cl. .................. 623/1.42; 424/78.08; 424/78.3; 424/422; 424/423; 424/425; 424/451; 424/457; 424/489; 424/490; 623/1.15; 623/1.46; 606/1

(58) Field of Classification Search ............. 424/78.08, 424/78.3, 422, 423, 425, 457, 451, 489, 490; 623/1.15, 1.42, 1.46; 606/1
See application file for complete search history.

(56) References Cited

U.S. PATENT DOCUMENTS

| | | | |
|---|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 4,226,243 A | 10/1980 | Shalaby et al. |
| 4,304,767 A | 12/1981 | Heller et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,380,299 A | 1/1995 | Fearnot et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,569,463 A | 10/1996 | Helmus et al. |

(Continued)

FOREIGN PATENT DOCUMENTS

DE           42 24 401           1/1994

(Continued)

OTHER PUBLICATIONS

U.S. Appl. No. 10/816,072, filed Mar. 31, 2004, Dugan et al.
Anonymous, *Cardiologists Draw / Up The Dream Stent*, Clinica 710:15 (Jun. 17, 1996), http://www.dialogweb.com/cgi/document?req=1061848202959, printed Aug. 25, 2003 (2 pages).
Anonymous, *Heparin/coated stents cut complications by 30%*, Clinica 732:17 (Nov. 18, 1996), http://www.dialogweb.com/cgi/document?req=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974/975 (Jun. 2000).
Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

(Continued)

*Primary Examiner*—Ana L Woodward
(74) *Attorney, Agent, or Firm*—Squire Sanders & Dempsey LLP

(57) ABSTRACT

Provided herein is a copolymer that includes a soft block (A) and a hard block (B) comprising a tyrosine di-peptide. The copolymer can be any of AB, ABA or BAB type block copolymers. The soft block can include a PEA polymer. A coating formed of the copolymer may also include a bioactive agent. The implantable device can be implanted in a patient to treat, prevent, or ameliorate a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, and/or tumor obstruction.

8 Claims, No Drawings

U.S. PATENT DOCUMENTS

| | | |
|---|---|---|
| 5,578,073 A | 11/1996 | Haimovich et al. |
| 5,581,387 A | 12/1996 | Cahill |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,759,205 A | 6/1998 | Valentini |
| 5,776,184 A | 7/1998 | Tuch |
| 5,783,657 A | 7/1998 | Pavlin et al. |
| 5,788,979 A | 8/1998 | Alt et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,849,859 A | 12/1998 | Acemoglu |
| 5,851,508 A | 12/1998 | Greff et al. |
| 5,854,376 A | 12/1998 | Higashi |
| 5,858,746 A | 1/1999 | Hubbell et al. |
| 5,861,387 A | 1/1999 | Labrie et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,879,713 A | 3/1999 | Roth et al. |
| 5,902,875 A | 5/1999 | Roby et al. |
| 5,905,168 A | 5/1999 | Dos Santos et al. |
| 5,910,564 A | 6/1999 | Gruning et al. |
| 5,914,387 A | 6/1999 | Roby et al. |
| 5,919,893 A | 7/1999 | Roby et al. |
| 5,925,720 A | 7/1999 | Kataoka et al. |
| 5,932,299 A | 8/1999 | Katoot |
| 5,955,509 A | 9/1999 | Webber et al. |
| 5,958,385 A | 9/1999 | Tondeur et al. |
| 5,962,138 A | 10/1999 | Kolluri et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,010,530 A | 1/2000 | Goicoechea |
| 6,011,125 A | 1/2000 | Lohmeijer et al. |
| 6,015,541 A | 1/2000 | Greff et al. |
| 6,033,582 A | 3/2000 | Lee et al. |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,120,491 A | 9/2000 | Kohn et al. |
| 6,120,536 A | 9/2000 | Ding et al. |
| 6,120,788 A | 9/2000 | Barrows |
| 6,120,904 A | 9/2000 | Hostettler et al. |
| 6,121,027 A | 9/2000 | Clapper et al. |
| 6,129,761 A | 10/2000 | Hubbell |
| 6,136,333 A | 10/2000 | Cohn et al. |
| 6,143,354 A | 11/2000 | Koulik et al. |
| 6,153,252 A | 11/2000 | Hossainy et al. |
| 6,159,978 A | 12/2000 | Myers et al. |
| 6,165,212 A | 12/2000 | Dereume et al. |
| 6,172,167 B1 | 1/2001 | Stapert et al. |
| 6,177,523 B1 | 1/2001 | Reich et al. |
| 6,180,632 B1 | 1/2001 | Myers et al. |
| 6,203,551 B1 | 3/2001 | Wu |
| 6,211,249 B1 | 4/2001 | Cohn et al. |
| 6,214,901 B1 | 4/2001 | Chudzik et al. |
| 6,231,600 B1 | 5/2001 | Zhong |
| 6,240,616 B1 | 6/2001 | Yan |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,365,172 B1 | 4/2002 | Barrows |
| 6,379,381 B1 | 4/2002 | Hossainy et al. |
| 6,387,379 B1 | 5/2002 | Goldberg et al. |
| 6,395,326 B1 | 5/2002 | Castro et al. |
| 6,419,692 B1 | 7/2002 | Yang et al. |
| 6,451,373 B1 | 9/2002 | Hossainy et al. |
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,511,748 B1 | 1/2003 | Barrows |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |

| | | | | | | |
|---|---|---|---|---|---|---|
| 6,565,659 | B1 | 5/2003 | Pacetti et al. | 2003/0028244 A1 | 2/2003 | Bates et al. |
| 6,572,644 | B1 | 6/2003 | Moein | 2003/0031780 A1 | 2/2003 | Chudzik et al. |
| 6,585,755 | B2 | 7/2003 | Jackson et al. | 2003/0032767 A1 | 2/2003 | Tada et al. |
| 6,585,765 | B1 | 7/2003 | Hossainy et al. | 2003/0036794 A1 | 2/2003 | Ragheb et al. |
| 6,585,926 | B1 | 7/2003 | Mirzaee | 2003/0039689 A1 | 2/2003 | Chen et al. |
| 6,605,154 | B1 | 8/2003 | Villareal | 2003/0040712 A1 | 2/2003 | Ray et al. |
| 6,616,765 | B1 | 9/2003 | Wu et al. | 2003/0040790 A1 | 2/2003 | Furst |
| 6,623,448 | B2 | 9/2003 | Slater | 2003/0059520 A1 | 3/2003 | Chen et al. |
| 6,625,486 | B2 | 9/2003 | Lundkvist et al. | 2003/0060877 A1 | 3/2003 | Falotico et al. |
| 6,645,135 | B1 | 11/2003 | Bhat | 2003/0065377 A1 | 4/2003 | Davila et al. |
| 6,645,195 | B1 | 11/2003 | Bhat et al. | 2003/0072868 A1 | 4/2003 | Harish et al. |
| 6,656,216 | B1 | 12/2003 | Hossainy et al. | 2003/0073961 A1 | 4/2003 | Happ |
| 6,656,506 | B1 | 12/2003 | Wu et al. | 2003/0083646 A1 | 5/2003 | Sirhan et al. |
| 6,660,034 | B1 | 12/2003 | Mandrusov et al. | 2003/0083739 A1 | 5/2003 | Cafferata |
| 6,663,662 | B2 | 12/2003 | Pacetti et al. | 2003/0097088 A1 | 5/2003 | Pacetti |
| 6,663,880 | B1 | 12/2003 | Roorda et al. | 2003/0097173 A1 | 5/2003 | Dutta |
| 6,666,880 | B1 | 12/2003 | Chiu et al. | 2003/0099712 A1 | 5/2003 | Jayaraman |
| 6,673,154 | B1 | 1/2004 | Pacetti et al. | 2003/0105518 A1 | 6/2003 | Dutta |
| 6,673,385 | B1 | 1/2004 | Ding et al. | 2003/0113439 A1 | 6/2003 | Pacetti et al. |
| 6,689,099 | B2 | 2/2004 | Mirzaee | 2003/0150380 A1 | 8/2003 | Yoe |
| 6,695,920 | B1 | 2/2004 | Pacetti et al. | 2003/0157241 A1 | 8/2003 | Hossainy et al. |
| 6,706,013 | B1 | 3/2004 | Bhat et al. | 2003/0158517 A1 | 8/2003 | Kokish |
| 6,709,514 | B1 | 3/2004 | Hossainy | 2003/0190406 A1 | 10/2003 | Hossainy et al. |
| 6,712,845 | B2 | 3/2004 | Hossainy | 2003/0207020 A1 | 11/2003 | Villareal |
| 6,713,119 | B2 | 3/2004 | Hossainy et al. | 2003/0211230 A1 | 11/2003 | Pacetti et al. |
| 6,716,444 | B1 | 4/2004 | Castro et al. | 2004/0018296 A1 | 1/2004 | Castro et al. |
| 6,723,120 | B2 | 4/2004 | Yan | 2004/0029952 A1 | 2/2004 | Chen et al. |
| 6,733,768 | B2 | 5/2004 | Hossainy et al. | 2004/0047978 A1 | 3/2004 | Hossainy et al. |
| 6,740,040 | B1 | 5/2004 | Mandrusov et al. | 2004/0047980 A1 | 3/2004 | Pacetti et al. |
| 6,743,462 | B1 | 6/2004 | Pacetti | 2004/0052858 A1 | 3/2004 | Wu et al. |
| 6,749,626 | B1 | 6/2004 | Bhat et al. | 2004/0052859 A1 | 3/2004 | Wu et al. |
| 6,753,071 | B1 | 6/2004 | Pacetti et al. | 2004/0054104 A1 | 3/2004 | Pacetti |
| 6,758,859 | B1 | 7/2004 | Dang et al. | 2004/0060508 A1 | 4/2004 | Pacetti et al. |
| 6,759,054 | B2 | 7/2004 | Chen et al. | 2004/0062853 A1 | 4/2004 | Pacetti et al. |
| 6,764,505 | B1 | 7/2004 | Hossainy et al. | 2004/0063805 A1 | 4/2004 | Pacetti et al. |
| 7,056,591 | B1 | 6/2006 | Pacetti et al. | 2004/0071861 A1 | 4/2004 | Mandrusov et al. |
| 7,166,680 | B2 | 1/2007 | Desnoyer et al. | 2004/0072922 A1 | 4/2004 | Hossainy et al. |
| 7,220,816 | B2 | 5/2007 | Pacetti et al. | 2004/0073298 A1 | 4/2004 | Hossainy |
| 7,390,497 | B2 | 6/2008 | Desnoyer et al. | 2004/0086542 A1 | 5/2004 | Hossainy et al. |
| 2001/0007083 | A1 | 7/2001 | Roorda | 2004/0086550 A1 | 5/2004 | Roorda et al. |
| 2001/0014717 | A1 | 8/2001 | Hossainy et al. | 2004/0096504 A1 | 5/2004 | Michal |
| 2001/0018469 | A1 | 8/2001 | Chen et al. | 2004/0098117 A1 | 5/2004 | Hossainy et al. |
| 2001/0020011 | A1 | 9/2001 | Mathiowitz et al. | 2005/0106204 A1 | 5/2005 | Hossainy et al. |
| 2001/0029351 | A1 | 10/2001 | Falotico et al. | 2005/0112171 A1 | 5/2005 | Tang et al. |
| 2001/0037145 | A1 | 11/2001 | Guruwaiya et al. | 2005/0137381 A1 | 6/2005 | Pacetti et al. |
| 2001/0051608 | A1 | 12/2001 | Mathiowitz et al. | 2005/0208091 A1 | 9/2005 | Pacetti |
| 2002/0005206 | A1 | 1/2002 | Falotico et al. | 2005/0245637 A1 | 11/2005 | Tang et al. |
| 2002/0007213 | A1 | 1/2002 | Falotico et al. | 2005/0265960 A1 | 12/2005 | Pacetti et al. |
| 2002/0007214 | A1 | 1/2002 | Falotico | 2005/0271700 A1 | 12/2005 | Desnoyer et al. |
| 2002/0007215 | A1 | 1/2002 | Falotico et al. | 2006/0034891 A1* | 2/2006 | Lawin et al. ............. 424/427 |
| 2002/0009604 | A1 | 1/2002 | Zamora et al. | 2006/0089485 A1 | 4/2006 | Desnoyer et al. |
| 2002/0016625 | A1 | 2/2002 | Falotico et al. | 2006/0115449 A1* | 6/2006 | Pacetti ............. 424/78.27 |
| 2002/0032414 | A1 | 3/2002 | Ragheb et al. | 2006/0115513 A1 | 6/2006 | Hossainy |
| 2002/0032434 | A1 | 3/2002 | Chudzik et al. | | | |
| 2002/0051730 | A1 | 5/2002 | Bodnar et al. | | FOREIGN PATENT DOCUMENTS | |
| 2002/0071822 | A1 | 6/2002 | Uhrich | | | |
| 2002/0077693 | A1 | 6/2002 | Barclay et al. | EP | 0 514 406 | 11/1992 |
| 2002/0082679 | A1 | 6/2002 | Sirhan et al. | EP | 0 604 022 | 6/1994 |
| 2002/0087123 | A1 | 7/2002 | Hossainy et al. | EP | 0 623 354 | 11/1994 |
| 2002/0091433 | A1 | 7/2002 | Ding et al. | EP | 0 665 023 | 8/1995 |
| 2002/0094440 | A1 | 7/2002 | Llanos et al. | EP | 0 701 802 | 3/1996 |
| 2002/0111590 | A1 | 8/2002 | Davila et al. | EP | 0 716 836 | 6/1996 |
| 2002/0120326 | A1 | 8/2002 | Michal | EP | 0 809 999 | 12/1997 |
| 2002/0123801 | A1 | 9/2002 | Pacetti et al. | EP | 0 832 655 | 4/1998 |
| 2002/0142039 | A1 | 10/2002 | Claude | EP | 0 850 651 | 7/1998 |
| 2002/0155212 | A1 | 10/2002 | Hossainy | EP | 0 879 595 | 11/1998 |
| 2002/0165608 | A1 | 11/2002 | Llanos et al. | EP | 0 910 584 | 4/1999 |
| 2002/0176849 | A1 | 11/2002 | Slepian | EP | 0 923 953 | 6/1999 |
| 2002/0183581 | A1 | 12/2002 | Yoe et al. | EP | 0 953 320 | 11/1999 |
| 2002/0188037 | A1 | 12/2002 | Chudzik et al. | EP | 0 970 711 | 1/2000 |
| 2002/0188277 | A1 | 12/2002 | Roorda et al. | EP | 0 982 041 | 3/2000 |
| 2003/0004141 | A1 | 1/2003 | Brown | EP | 1 023 879 | 8/2000 |
| 2003/0028243 | A1 | 2/2003 | Bates et al. | EP | 1 192 957 | 4/2002 |

| | | |
|---|---|---|
| EP | 1 273 314 | 1/2003 |
| JP | 2001/190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| SU | 0 301 856 | 2/1989 |
| SU | 0 396 429 | 11/1990 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |

OTHER PUBLICATIONS

Aoyagi et al., *Preparation of cross/linked aliphatic polyester and application to thermo/responsive material*, Journal of Controlled Release 32:87/96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259/1274 (Oct. 1991).

Chandrasekar et al., *Coronary Artery Endothelial Protection After Local Delivery of 17β/Estradiol During Balloon Angioplasty in a Porcine Model: A Potential New Pharmacologic Approach to Improve Endothelial Function*, J. of Am. College of Cardiology, vol. 38, No. 5, (2001) pp. 1570/1576.

Chung et al., *Inner core segment design for drug delivery control of thermo/responsive polymeric micelles*, Journal of Controlled Release 65:93/103 (2000).

De Lezo et al., *Intracoronary Ultrasound Assessment of Directional Coronary Atherectomy: Immediate and Follow/Up Findings*, JACC vol. 21, No. 2, (1993) pp. 298/307.

Dev et al., *Kinetics of Drug Delivery to the Arterial Wall Via Polyurethane/Coated Removable Nitinol Stent: Comparative Study of Two Drugs*, Catheterization and Cardiovascular Diagnosis 34:272/278 (1995).

Dichek et al., *Seeding of Intravascular Stents with Genetically Engineered Endothelial Cells*, Circ. 80(5):1347/1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701/1), Abstract (Feb. 1994).

Helmus, *Overview of Biomedical Materials*, MRS Bulletin, pp. 33/38 (Sep. 1991).

Herdeg et al., *Antiproliferative Stent Coatings: Taxol and Related Compounds*, Semin. Intervent. Cardiol. 3:197/199 (1998).

Huang et al., *Biodegradable Polymers Derived from Aminoacids*, Macromol. Symp. 144, 7/32 (1999).

Inoue et al., *An AB block copolymer of oligo(methyl methacrylate) and poly(acrylic acid) for micellar delivery of hydrophobic drugs*, Journal of Controlled Release 51:221/229 (1998).

Kataoka et al., *Block copolymer micelles as vehicles for drug delivery*, Journal of Controlled Release 24:119/132 (1993).

Katsarava et al., *Amino Acid/Based Bioanalogous Polymers. Synthesis and Study of Regular Poly(ester amide)s Based on Bis($\alpha$/amino acid)$\alpha$,$\omega$/Alkylene Diesters, and Aliphatic Dicarbolic Acids*, Journal of Polymer Science, Part A: Polymer Chemistry, 37(4), 391/407 (1999).

Levy et al., *Strategies for Treating Arterial Restenosis Using Polymeric Controlled Release Implants*, Biotechnol. Bioact. Polym. [Proc. Am. Chem. Soc. Symp.], pp. 259/268 (1994).

Liu et al., *Drug release characteristics of unimolecular polymeric micelles*, Journal of Controlled Release 68:167/174 (2000).

Marconi et al., *Covalent bonding of heparin to a vinyl copolymer for biomedical applications*, Biomaterials 18(12):885/890 (1997).

Matsumaru et al., *Embolic Materials for Endovascular Treatment of Cerebral Lesions*, J. Biomater. Sci. Polymer Edn 8(7):555/569 (1997).

Miyazaki et al., *Antitumor Effect of Implanted Ethylene/Vinyl Alcohol Copolymer Matrices Containing Anticancer Agents on Ehrlich Ascites Carcinoma and P388 Leukemia in Mice*, Chem. Pharm. Bull. 33(6)2490/2498 (1985).

Miyazawa et al., *Effects of Pemirolast and Tranilast on Intimal Thickening After Arterial Injury in the Rat*, J. Cardiovasc. Pharmacol., pp. 157/162 (1997).

Moreno et al., *Macrophage Infiltration Predicts Restenosis After Coronary Intervention in Patients with Unstable Angina*, Circulation, vol. 94, No. 12, (1996) pp. 3098/3102.

Nordrehaug et al., *A novel biocompatible coating applied to coronary stents*, EPO Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081/1087 (Dec. 1998).

Oikawa et al., *Mechanisms of Acute Gain and Late Lumen Loss After Atherectomy in Different Preintervention Arterial Remodeling Patterns*, The Am. J. of Cardilogy, vol. 89, (2002) pp. 505/510.

Ozaki et al., *New Stent Technologies*, Progress in Cardiovascular Diseases, vol. XXXIX(2):129/140 (Sep./Oct. 1996).

Pechar et al., *Poly(ethylene glycol) Multiblock Copolymer as a Carrier of Anti/Cancer Drug Doxorubicin*, Bioconjucate Chemistry 11(2):131/139 (Mar./Apr. 2000).

Peng et al., *Role of polymers in improving the results of stenting in coronary arteries*, Biomaterials 17:685/694 (1996).

Saotome, et al., *Novel Enzymatically Degradable Polymers Comprising $\alpha$/Amino Acid, 1,2/Ethanediol, and Adipic Acid*, Chemistry Letters, pp. 21/24, (1991).

Scully et al., *Effect of a heparan sulphate with high affinity for antithrombin III upon inactivation of thrombin and coagulaton Factor Xa*, Biochem J. 262, (1989) pp. 651/658.

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590/596 (Jul. 1994).

Virmani et al., *Lessons From Sudden Coronary Death a Comprehensive Morphological Classification Scheme for Atherosclerotic Lesions*, Arterioscler Thromb Vasc Biol. (2000) pp. 1262/1275.

Wilensky et al., *Methods and Devices for Local Drug Delivery in Coronary and Peripheral Arteries*, Trends Cardiovasc. Med. 3(5):163/170 (1993).

Yokoyama et al., *Characterization of physical polymeric entrapment and chemical conjugation of adriamycin in polymeric micelles and their design for in vivo delivery to a solid tumor*, Journal of Controlled Release 50:79/92 (1998).

\* cited by examiner

POLY(ESTER AMIDE) BLOCK COPOLYMERS

CROSS-REFERENCE TO RELATED APPLICATION

This is a continuation application of U.S. application Ser. No. 11/023,837, filed Dec. 27, 2004 now U.S. Pat. No. 7,419,504, the teaching of which is incorporated herein in its entirety by reference.

BACKGROUND OF THE INVENTION

1. Field of the Invention

This invention generally relates to poly(ester amide) block copolymers useful for forming a bioabsorbable device such as a stent or for coating an implantable device such as a drug-delivery stent.

2. Description of the Background

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain vascular patency.

Stents are used not only as a mechanical intervention but also as a vehicle for providing pharmacological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Pharmacological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent.

Accordingly, there is a need to have stent coatings with improved biological compatibility and improved mechanical properties.

The embodiments of the present invention provide for polymers and combination of polymers for coating stents and other implantable medical devices, where the polymers forming the coatings are biologically compatible and absorbable.

SUMMARY OF THE INVENTION

In an aspect of the present invention, provided herein is a copolymer that includes a soft block (A) which can be a poly(ester amide) (PEA) block (A) and another block (B). The copolymer can be any of AB, ABA, and BAB type block copolymer. By varying the relative amount of the soft block (e.g. PEA block) and the hard block, one can obtain a copolymer with a $T_g$ for mechanical integrity in drug-delivery stent applications.

The copolymer can be used alone or optionally in combination with a biobeneficial material and/or a biocompatible polymer to form a coating on an implantable device or to form the implantable device itself. When the copolymer is used in combination with a biobeneficial material, the copolymer and the biobeneficial material can be co-deposited or applied in sequence during the coating process.

The implantable device or the coating may also include a bioactive agent. Exemplary bioactive agents include, but are not limited to, paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, prodrugs thereof, co-drugs thereof, and combinations thereof. The implantable device can be implanted in a patient to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

DETAILED DESCRIPTION

Poly(Ester Amide) Block Copolymer

In one aspect of the present invention, provided herein is a copolymer that includes a soft block which can be a poly(ester amide) (PEA) block (A) and a hard block (B) derived from a biocompatible polymer. The copolymer can be any of AB, ABA, and BAB type block copolymer. By varying the relative amount of the soft block (e.g., a PEA block) and the hard block, one can obtain a copolymer with a glass transition temperature ($T_g$) for mechanical integrity in drug-delivery stent applications.

The terms "hard" and "soft" are relative terms and, as used herein, refer to mechanical strength and toughness of the block copolymer defined herein. The term "hard block" refers to the block that has a higher mechanical strength and toughness whereas the term "soft block" refers to the block that has a lower mechanical strength and toughness. Generally, the hard block in a block copolymer has a glass $T_g$ higher than the $T_g$ of the soft block. However, the hard block in a block copolymer described herein may sometimes have a $T_g$ approximately the same as or lower than the $T_g$ of a soft block.

The copolymer can be used alone or optionally in combination with a biobeneficial material and/or a biocompatible polymer to form a coating on an implantable device or to form the implantable device itself. When the copolymer is used in combination with a biobeneficial material, the copolymer and the biobeneficial material can be co-deposited or applied in sequence during the coating process.

The implantable device or the coating may also include a bioactive agent. Exemplary bioactive agents include, but are not limited to, paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, prodrugs thereof, co-drugs thereof, and combinations thereof. The implantable device can be implanted in a patient to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

A. Poly(Ester Amide) Block (A)

Poly(ester amide), as used herein, encompasses any polymer having both ester and amide groups in its backbone. In one embodiment, the PEA is formed of a diacid and another moiety having both amino and hydroxyl functionalities. One of such PEA is described in, e.g., U.S. Pat. No. 6,503,538, B1. The diacid is preferably a C2-C12 diacid, aliphatic or with unsaturation. The amino acid can be, for example, glycine, valine, alanine, proline, glutamine, methionine, leucine, isoleucine, or phenylalanine. An optional second amino acid may be included. The second amino acid can be, for example, lysine, tyrosine, tryptophan, arginine, histidine, glutamic acid, aspartic acid, threonine, serine, or cysteine. The second amino acid may contain a side group to enable the attachment of pharmacologically active compounds or property modifiers. PEA polymers with various thermal properties can be readily prepared by varying these components during synthesis.

PEA can be made by condensation polymerization utilizing, among others, diamino subunits and dicarboxylic acids (Scheme I). In Scheme I, the dicarboxylic acids are converted to an active di-p-nitrophenyl derivative. As shown in Scheme I, when the dicarboxylic acid and the diamino subunits are used stoichiometrically, the PEA formed would have one terminal carboxylic acid group and one amino group. When the dicarboxylic acid and the diamino subunits are not used at a ratio of 1:1, the PEA thus formed can have end groups in favor of the carboxylic acid group, if the dicarboxylic acid subunit is used more than the diamino subunit, or in favor of the amino group, if the diamino subunit is used more than the dicarboxylic acid subunit. Accordingly, the PEA molecule would have reactive carboxylic acid or amino end groups.

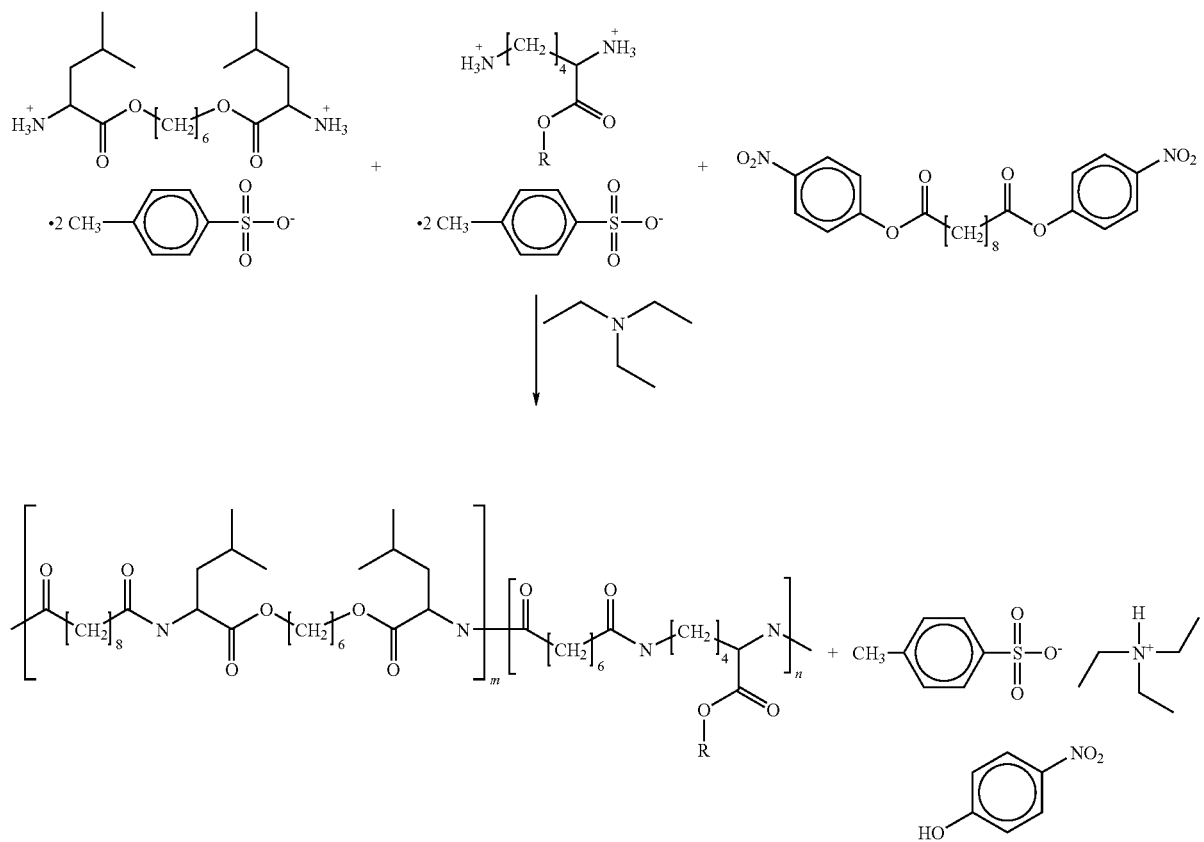

Scheme I

The soft block can also be derived from PEA having another moiety attached thereto, e.g., poly(ethylene glycol) (PEG), 4-amino-2,2,6,6-tetramethylpiperidine-1-oxyl (4-amino-TEMPO), or a combination thereof. In some embodiments, the soft block can be PEA, PEA-PEG, PEA-4-amino-TEMPO, PEG, or a combination thereof.

B. Hard Block (B)

The hard blocks of the PEA block copolymer can be formed of a material having a higher Tg than PEA. In some embodiments, the material is one or more biocompatible polymer. Exemplary biocompatible polymers include, but are not limited to, poly(D,L-lactic acid) (PDLLA, polyglycolic acid (PGA), poly(D,L-lactic acid-co-glycolic acid) (PDLLG), glycerol-sebacic acid, polytyrosine carbonate, polytyrosine, tyrosine oligomer, or tyrosine di-peptide, poly (3-hydroxybutyrate) (PHB), poly(3-hydroxybutyrate-co-3-hydroxyvalerate) (PHBV), poly(3-hydroxyvalerate) (PHV), polyphosphazene, or combinations thereof. The polymer forming the hard block may also include functional groups such as OH, $NH_2$, COOH, SH, positive or negative charge, $SO_3H$, $SO_4H$, halo groups or PEG.

In some embodiments, the hard block is a tyrosine di-peptide. An exemplary tyrosine di-peptide block has a structure of

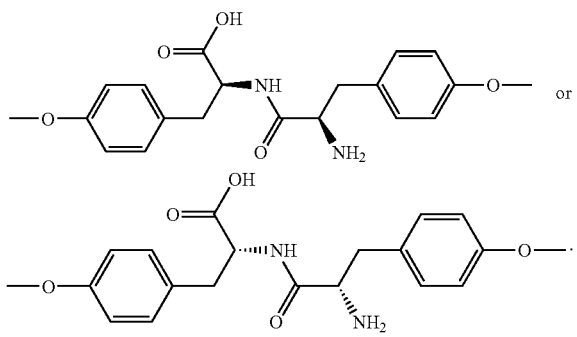

In some embodiments, the tyrosine di-peptide block can be formed of racemic tyrosine. This di-peptide structure is relatively rigid and can increase the $T_g$ and the tensile modulus of the copolymer. In addition, the carboxyl group and the primary amine group on the block can conjugate other reactive moieties such as —COOH, —$NH_2$, aldehyde, keto, hydroxyl, thiol, acyl, and other moieties so as to allow the attachment of functional molecules such as a drug molecule for forming a prodrug, heparin for imparting anti-thrombonic properties to the copolymer, iodo or bromo containing molecules for imparting radioopacity to the copolymer, and other marker compounds for diagnostic uses. The chemistry of forming a prodrug via an ester group, a Schiff base group or other groups that can release the drug molecule under in vivo conditions is described in U.S. application Ser. No. 10/871,658. The chemistry of attaching heparin to a polymer is described in U.S. application Ser. No. 10/857,141. The teachings of both U.S. application Ser. Nos. 10/871,658 and 10/871,658 are incorporated herein by reference.

In some embodiments, the iodo or bromo compound can have a general formula X—Ar—R where X is I or Br and R is a reactive moiety. For example, the iodo or bromo compound can have a structure of

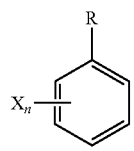

where X can be (1) an organic group $R_1$, provided that $R_1$ has one or more halo groups such as iodo or bromo groups, (2) halo groups such as iodo or bromo groups, or (3) combinations thereof, where R and $R_1$ taken independently can be any chemical grouping having one or more reactive groups capable of conjugating to the carboxyl group or amino group of the tyrosine di-peptide block, which can be, for example, carboxyl groups, aldehyde groups, ester, amino groups, alcohol, thiol, PEG, a leaving group such as tosylate or mesylate, and where n is a positive integer such as 1, 2, or 3.

The tyrosine di-peptide block can be any structural derivative of the tyrosine di-peptide. For example, the tyrosine di-peptide can be desamine tyrosyl-tyrosine di-peptide, desamino tyrosyl-tyrosine hexyl ester (DTH), desamino tyrosyl-tyrosine palmityl ester (DTP), n-benzyloxycarbonyl-tyrosyl-tyrosine hexyl ester (z-TTH), or combinations thereof. Other tyrosine di-peptides are provided in Biomedical Polymers: Designed-to-degrade Systems, Shalaby W. Shalaby (Editor), 1994. Note, in z-TTH, the benzoyl protected group can be reacted to conjugate biobeneficial moieties.

In some embodiments, the tyrosine di-peptide can be randomly incorporated into a PEA polymer. The $NH_2$ and/or COOH groups on the tyrosine di-peptide can be used to conjugate the bromo or iodo compound, a biobeneficial moiety, and/or a bioactive agent described herein.

Biocompatible Polymer

The PEA block copolymer described herein can be used alone or in combination with a biocompatible polymer, optionally with biobeneficial material and/or a bioactive agent to form a bioabsorbable device such as stent or a coating on an implantable device such as a stent. The biocompatible polymer can be any biocompatible polymer known in the art, which can be biodegradable or nondegradable. Representative examples of polymers that can be used to coat an implantable device in accordance with the present invention include, but are not limited to, poly(ester amide), ethylene vinyl alcohol copolymer (commonly known by the generic name EVOH or by the trade name EVAL), poly(3-hydroxyvalerate), poly(L-lactic acid), polycaprolactone, poly(lactide-co-glycolide), poly(3-hydroxybutyrate), poly(3-hydroxybutyrate-co-3-hydroxyvalerate), polydioxanone, polyorthoester, polyanhydride, poly(glycolic acid), poly(D,L-lactic acid), poly(D,L-lactide-co-glycolide) (PDLLAGA), poly (glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alpha-olefin copolymers, acrylic polymers and copolymers, vinyl halide polymers and copolymers, such as polyvinyl chloride, polyvinyl ethers, such as polyvinyl methyl ether; polyvinylidene halides, such as vinylidene fluoride based home or copolymer under the trade name Solef™ or Kynar™, for example, polyvinylidene fluoride (PVDF) or poly(vinylidene-co-hexafluoropropylene) (PVDF-co-HFP) and polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, or combinations thereof.

The biocompatible polymer can provide a controlled release of a bioactive agent, if included in the coating and/or if binding the bioactive agent to a substrate, which can be the surface of an implantable device or a coating thereon. Controlled release and delivery of bioactive agent using a polymeric carrier has been extensively researched in the past several decades (see, for example, Mathiowitz, Ed., Encyclopedia of Controlled Drug Delivery, C.H.I.P.S., 1999). For example, PLA based drug delivery systems have provided controlled release of many therapeutic drugs with various degrees of success (see, for example, U.S. Pat. No. 5,861,387 to Labrie, et al.). The release rate of the bioactive agent can be controlled by, for example, selection of a particular type of biocompatible polymer, which can provide a desired release profile of the bioactive agent. The release profile of the bioactive agent can be further controlled by selecting the molecular weight of the biocompatible polymer and/or the ratio of the biocompatible polymer to the bioactive agent. One of ordinary skill in the art can readily select a carrier system using a biocompatible polymer to provide a controlled release of the bioactive agent.

A preferred biocompatible polymer is a polyester, such as one of PLA, PLGA, PGA, PHA, poly(3-hydroxybutyrate) (PHB), poly(3-hydroxybutyrate-co-3-hydroxyvalerate), poly((3-hydroxyvalerate), poly(3-hydroxyhexanoate), poly(4-hydroxybutyrate), poly(4-hydroxyvalerate), poly(4-hydroxyhexanoate), and a combination thereof, and polycaprolactone (PCL).

Bioactive Agents

The PEA copolymers disclosed herein can form a coating or a bioabsorbable device such as a bioabsorbable stent with one or more bioactive agents. These bioactive agents can be any therapeutic, prophylactic, or diagnostic agents. These agents can have anti-proliferative or anti-inflammatory properties or can have other properties such as antineoplastic, antiplatelet, anti-coagulant, anti-fibrin, antithrombonic, anti-mitotic, antibiotic, antiallergic, antioxidant as well as cytostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy) ethyl-rapamycin (everolimus), and its functional or structural derivatives, paclitaxel and its functional and structural derivatives. Examples of rapamycin derivatives include methyl rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, bioactive RGD, and genetically engineered epithelial cells. The foregoing substances can also be used in the form of prodrugs or co-drugs thereof. The foregoing substances are listed by way of example and are not meant to be limiting. Other active agents which are currently available or that may be developed in the future are equally applicable.

The dosage or concentration of the bioactive agent should be less than the level at which the bioactive agent produces toxic effects and greater than the level at which non-therapeutic results are obtained. The dosage or concentration of the bioactive agent can depend upon factors such as the particular circumstances of the patient, the nature of the trauma; the nature of the therapy desired, the time over which the ingredient administered resides at the vascular site, and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Method of Use

In accordance with embodiments of the invention, a coating of the various described embodiments can be formed on an implantable device or prosthesis, e.g., a stent. For coatings including one or more active agents, the agent will retain on the medical device such as a stent during delivery and expansion of the device, and released at a desired rate and for a predetermined duration of time at the site of implantation.

Preferably, the medical device is a stent. A stent described herein is useful for a variety of medical procedures, including, by way of example, treatment of obstructions caused by tumors in bile ducts, esophagus, trachea/bronchi and other biological passageways. A stent described herein is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A coating for an implantable device comprising a copolymer and a drug, wherein the copolymer comprises a soft block (A) and a hard block (B) comprising tyrosine di-peptide, wherein the soft block (A) has a glass transition temperature ($T_g$) lower than that of the hard block, and
wherein the soft block (A) comprises a poly(ester amide).

2. The coating of claim 1 wherein the drug is selected from the group consisting of paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, progenitor cell capturing antibody, prohealing drugs, prodrugs thereof, co-drugs thereof, and a combination thereof.

3. The coating of claim 1, wherein the tyrosine di-peptide has a structure of

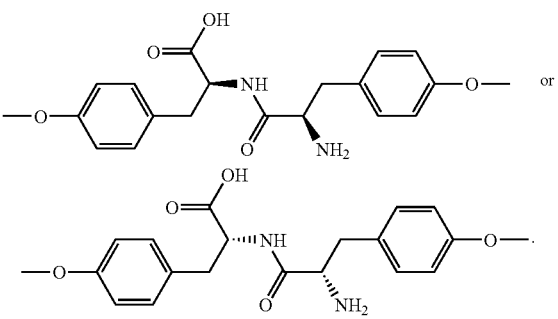

4. A implantable device comprising a coating, the coating comprising a copolymer and a drug, wherein the copolymer comprises a soft block (A) and a hard block (B) comprising tyrosine di-peptide, wherein the soft block (A) has a glass transition temperature ($T_g$) lower than that of the hard block, and
wherein the soft block (A) comprises a poly(ester amide).

5. The implantable device of claim 4, wherein the drug is selected from the group consisting of paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, progenitor cell capturing antibody, prohealing drugs, prodrugs thereof, co-drugs thereof, and a combination thereof.

6. The implantable device of claim 5, which is a stent.

7. The implantable device of claim 4, which is a stent.

8. The implantable device of claim 4, wherein the tyrosine di-peptide has a structure of

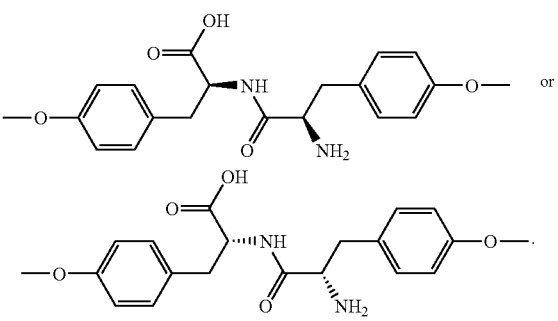

* * * * *